(12) United States Patent
Harder et al.

(10) Patent No.: US 8,425,835 B2
(45) Date of Patent: *Apr. 23, 2013

(54) ENDOPROSTHESIS

(75) Inventors: Claus Harder, Uttenreuth (DE); Bodo Gerold, Himmelstadt (DE); Heinz Mueller, Erlangen (DE); Bernd Heublein, Hannover (DE)

(73) Assignee: Biotronik VI Patent AG (CH)

( * ) Notice: Subject to any disclaimer, the term of this patent is extended or adjusted under 35 U.S.C. 154(b) by 2625 days.

This patent is subject to a terminal disclaimer.

(21) Appl. No.: 10/706,717

(22) Filed: Nov. 11, 2003

(65) Prior Publication Data

US 2004/0098108 A1   May 20, 2004

(30) Foreign Application Priority Data

Nov. 13, 2002  (DE) .................................. 102 53 634

(51) Int. Cl.
*C22C 23/00*   (2006.01)

(52) U.S. Cl.
USPC ........................................................ 420/402

(58) Field of Classification Search ................... 623/1.1, 623/1.15, 1.16, 1.18, 1.2, 1.38, 1.49; 420/402, 420/414

See application file for complete search history.

(56) References Cited

U.S. PATENT DOCUMENTS

| | | | | |
|---|---|---|---|---|
| 2,219,056 | A | * | 10/1940 | Sauerwald et. al. .......... 420/402 |
| 3,687,135 | A | | 8/1972 | Stroganov et al. |
| 4,401,621 | A | * | 8/1983 | Unsworth et al. ............ 420/403 |
| 6,206,916 | B1 | | 3/2001 | Furst |
| 6,287,332 | B1 | | 9/2001 | Bolz et al. |
| 6,676,697 | B1 | * | 1/2004 | Richter ......................... 623/1.16 |
| 6,979,347 | B1 | * | 12/2005 | Wu et al. ...................... 623/1.15 |
| 2002/0004060 | A1 | * | 1/2002 | Heublein et al. .............. 424/422 |
| 2003/0129074 | A1 | * | 7/2003 | Bronfin et al. ................ 420/406 |
| 2004/0241036 | A1 | * | 12/2004 | Meyer-Lindenberg et al. ............................. 420/405 |

FOREIGN PATENT DOCUMENTS

JP   57210946   12/1982
JP   2001511049   8/2001

OTHER PUBLICATIONS

Metallovedenie i Termicheskaya Obrabotka Metallo, 1988, No. 2, pp. 29-31.
Keikinzoku Gakkai Taikai Koen Gaiyo (Summary of lecture given at a conference of The Japan Institute of Light Metals), 2001, vol. 101, pp. 53-54.
William Unsworth, Competitive Advances in Metals and Processes, International SAMPE Metals and Metals Processing Conferrence Series, 1987, vol. 1, pp. 69-78.
W. Unsworth, Magnesium, 1989, vol. 18, No. 3, pp. 1-8.
Keikinzoku Gakkai Taikai Koen Gaiyo (Summary of lecture given at a conference of the Japan Institute of Light Metals), 1993, vol. 84, pp. 349-350.
Journal of the American College of Cardiology, Feb. 2000, vol. 35, No. 2, Suppl. 1, pp. 14A-15A, 1041-1090.
Haferkamp et al.; Alloy Development, Processing and Applications in Magnesium Lithium Alloys, Materials Transactions, 2001, vol. 42, No. 7, pp. 1160-1166.
English Translation of Japanese Official Letter, 2011.

* cited by examiner

*Primary Examiner* — Melanie Tyson
(74) *Attorney, Agent, or Firm* — Hahn Loeser & Parks LLP; John J. Cunniff

(57) ABSTRACT

An endoprosthesis includes a carrier structure which contains a metallic material. The metallic material contains a magnesium alloy of the following composition: magnesium: >90%, yttrium: 3.7%-5.5%, rare earths: 1.5%-4.4% and balance: <1%.

37 Claims, 2 Drawing Sheets

ENDOPROSTHESIS

The invention concerns an endoprosthesis having a carrier structure which contains a metallic material. The invention concerns in particular intraluminal endoprostheses such as stents.

BACKGROUND OF THE ART

The purpose of many endoprostheses is to implement a support function in the interior of the body of a patient. Accordingly endoprostheses are designed to be implantable and have a carrier structure which ensures the support function. Implants of metallic materials are known. The choice of metals as the material for the carrier structure of an implant of that nature is based in particular on the mechanical properties of metals.

In some case, particularly in the case of such intraluminal endoprostheses as stents, a durable support function afforded by the endoprosthesis is not required. Rather, in some of those situations of use, the body tissue can recover in the presence of the support prosthesis in such a way that there is no need for an ongoing supporting action by the prosthesis. That has led to the idea of making such prostheses from bioresorbable material.

In particular, German published patent application DE 197 31 021, co-invented by one of the present inventors, discloses a bioresorbable metal stent, the material of which, as its main constituent, contains magnesium, iron or zinc.

In particular metallic stents are known in large numbers. One of the main areas of use of such stents is permanently dilating and holding open vessel constrictions, in particular constrictions (stenoses) of the coronary vessels. In addition, aneurism stents are also known, which afford a support function for a damaged vessel wall. Stents of that kind generally have a peripheral wall of sufficient carrying strength to hold the constricted vehicle open to the desired amount. In order to permit an unimpeded flow of blood through the stent it is open at both ends. The supporting peripheral wall is generally formed by a lattice-like carrier structure which makes it possible for the stent to be introduced in a compressed condition when it is of small outside diameter to the constriction to be treated in the respective vessel and there expanded for example by means of a balloon catheter to such a degree that the vessel in the presence of the stent, after removal of the balloon catheter, is of the desired enlarged inside diameter. Basically therefore the stent is subject to the requirement that its carrier structure in the expanded condition affords a sufficient carrying strength to hold the vessel open. In order to avoid unnecessary vessel damage it is also desirable that, after expansion and after removal of the balloon, the stent only slightly elastically springs back (recoil) in order to have to expand the stent upon expansion thereof only as little as possible beyond the desired final diameter. Further criteria which are desirable in relation to a stent are for example uniform surface coverage, a structure which allows a certain degree of flexibility in relation to the longitudinal axis of the stent, and the like.

Besides the desired mechanical properties of a stent as far as possible it should interact with the body tissue at the implantation location in such a way that renewed vessel constrictions do not occur, in particular vessel constrictions caused by the stent itself. Re-stenosis (re-constriction of the vessel) should be avoided as much as possible. It is also desirable if the stent is as far as possible responsible for no or only a very slight inflammatory effect. In regard to a biodegradable metal stent it is moreover desirable that the decomposition products of the metal stent as far as possible have little negative physiological effects and if possible even positive physiological effects.

SUMMARY OF THE INVENTION

With that background in mind the object of the present patent application is to optimize an endoprosthesis of the kind set forth in the opening part of this specification in respect of the properties thereof.

In accordance with the invention that object is attained by an endoprosthesis of the kind set forth in the opening part of this specification, the metallic material of which contains a magnesium alloy of the following composition:

| | |
|---|---|
| Magnesium: | >90% |
| Yttrium: | 3.7%-5.5% |
| Rare earths: | 1.5%-4.4% and |
| Balance: | <1% |

That composition is based on the unexpected realization that an endoprosthesis which entirely or partially consists of the specified magnesium alloy satisfies many of the requirements involved in a quite particular positive fashion, in regard to the many different desirable properties. Besides the mechanical requirements, a material often entirely or partially consisting of the specified magnesium alloy also satisfies the further physiological properties, that is to say a slight inflammatory effect and sustained prevention of tissue growth such as for example re-stenoses. In actual fact tests have shown that the decomposition products of the specified magnesium alloy have only few or indeed no negative physiological effects but prima facie even positive properties. Therefore the specified magnesium alloy, among the large number of conceivable materials, represents an unexpectedly lucky choice.

Preferably the yttrium proportion of the magnesium alloy is between 4% and 5%. The proportion of rare earths in the magnesium alloy is preferably between 1.5% and 4%, a preferred rare earth element being neodymium. The balance proportion in the magnesium alloy of below 1% is preferably formed for the major part by zirconium and in addition possibly lithium.

By virtue of the extremely positive properties of the specified magnesium alloy the carrier structure of the endoprosthesis preferably entirely consists of the magnesium alloy.

The material of the carrier structure is preferably extruded. It has been found that processing of the material influences the physiological effect thereof. In that sense a preferred carrier structure is one which has the following physiological properties in appropriately known cell tests: in the vitality test MTS over 70% absorption at 490 nm in relation to smooth muscle cells (coronary endothelium cells) with 100%, that is to say a cell survival rate of over 70% upon cultivation of the cells with an eluate of the material of the carrier structure in comparison with untreated cells. In the proliferation test with BrdU (bromodeoxyuridine) the procedure gives a proliferation inhibition effect at below 20% with respect to untreated smooth muscle cells, that is to say under the influence of the magnesium alloy of the carrier structure the number of cells fluorescing by virtue of the absorption of BrdU is 20% with respect to a totality of 100% in the comparative test with untreated muscle cells. While for example extruded carrier structures consisting of the magnesium alloy have those physiological properties, it has been found that a cast carrier structure does not have those properties. Therefore those physiological properties are at least in part governed by the production process and are not necessarily inherent properties of the magnesium alloy. An influencing factor is also the heat treatment of the magnesium alloy during processing to give the finished carrier structure.

The endoprosthesis is preferably in the form of an intraluminal endoprosthesis. A particularly preferred endoprosthesis is one which is in the form of a stent, more specifically in particular in the form of a coronary stent or in the form of a peripheral stent. Coronary stents which contain the said magnesium alloy have shown in tests a sum of unexpectedly positive properties.

Particularly for a carrier structure for stents, it is appropriate for the carrier structure to be designed in per se known manner either in the form of a self-expanding carrier structure or in the form of a balloon-expandable carrier structure. A balloon-expandable carrier structure can involve in particular manufacture from a tube which is cut for example by means of a laser. The option that presents itself for a self-expanding carrier structure of magnesium alloy is a wire stent formed from wire which contains the magnesium alloy.

The carrier structure is preferably of a lattice-like nature and is formed by legs and by radial openings surrounded by the legs. Those legs are preferably of such similar cross-sectional areas that the ratio of largest to smallest cross-sectional area is smaller than 2. Similar leg cross-sectional areas provide that the implant is approximately uniformly rapidly broken down in all regions.

Legs in which the ratio of the largest to the smallest minimum cross-section—in the sense of a respectively smallest diameter—is less than 3 also serve for uniform breakdown of the implant.

In the case of a preferred configuration of the stent consisting of leg rings which are connected by connecting legs, the connecting legs are preferably of a smaller cross-sectional area or a smaller minimum diameter than the legs which form the leg rings. That provides that the connecting legs are broken down in the body of a patient more rapidly than the leg rings. The consequence of that in turn is that axial flexibility of the stent due to breakdown of the connecting legs increases more rapidly than the support force of the stent decreases as a consequence of the breakdown of the leg rings. That feature of making connecting legs thinner in comparison with supporting legs is of independent inventive significance not only in connection with the magnesium stent which is of interest here but in connection with any kind of bioresorbable stent.

Finally endoprostheses are preferred which bear a physiologically active material and which in particular are coated at least with a drug.

BRIEF DESCRIPTIONS OF THE DRAWINGS

The invention will now be described in greater detail by means of an embodiment with reference to the Figures in which.

DETAILED DESCRIPTION OF A PREFERRED EMBODIMENT

Figure 1:
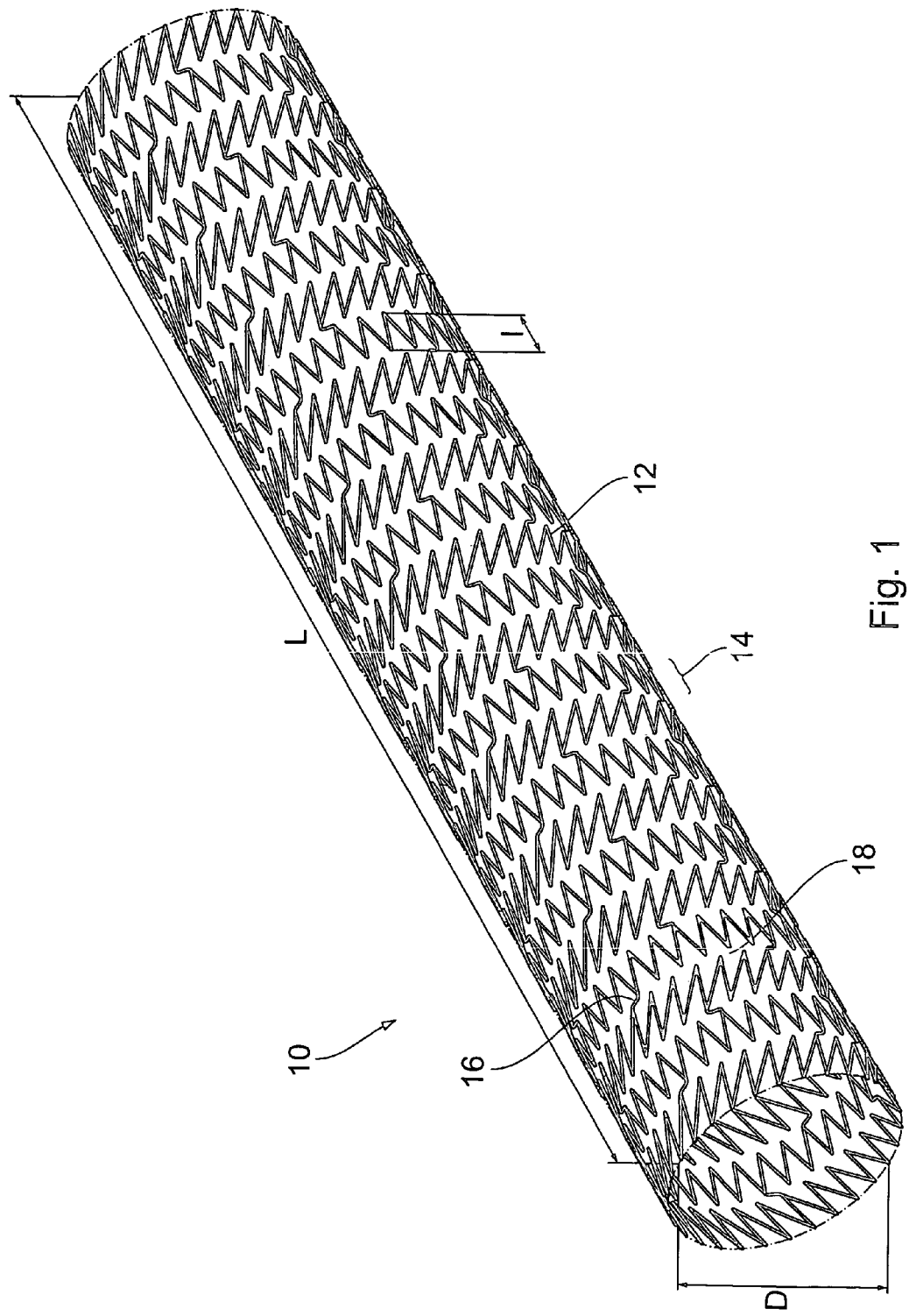
FIG. 1 shows a diagrammatic view of an endoprosthesis in the form of a stent.

FIG. 1 shows an endoprosthesis as an endoluminal prosthesis in the form of a stent having a carrier structure 10. The stent and its carrier structure 10 are in the form of a hollow body which is open at its ends and the peripheral wall of which is formed by the carrier structure 10 which in turn is formed by partially folded legs 12. The legs 12 form support portions 14 which are each formed by a leg 12 which is closed in an annular configuration in the longitudinal direction and which is folded in a zig-zag or meander-shaped configuration.

The carrier structure 10 of the stent is formed by a plurality of such support portions 12 which occur in succession in the longitudinal direction. The support portions or leg rings 14 are connected together by way of connecting legs 16. Each two connecting legs 16 which are mutually adjacent in the peripheral direction and the parts, which are in mutually opposite relationship between those connecting legs 16, of the leg rings or support portions 14 define a mesh 18 of the stent 10. Such a mesh 18 is shown emphasized in FIG. 1. Each mesh 18 encloses a radial opening in the peripheral wall or the carrier structure of the stent 10.

Each leg ring 14 has between some three and six connecting legs 16 which are distributed equally over the periphery of the stent 10 and which respectively connect a leg ring 14 to the adjacent leg ring 14. Accordingly the stent 10 has between three and six respective meshes in the peripheral direction between two support portions 14.

The stent 10 is expandable in the peripheral direction by virtue of the folding of the legs 12. That is effected for example by means of a per se known balloon catheter which at its distal end has a balloon which is expandable by means of a fluid. The stent is crimped onto the deflated balloon, in the compressed condition. Upon expansion of the balloon both the balloon and also the stent 10 are enlarged. The balloon can then be deflated again and the stent 10 is released from the balloon. In that way the catheter can serve simultaneously for introducing the stent 10 into a blood vessel and in particular into a constricted coronary vessel and also for expanding the stent at that location.

Figure 2:
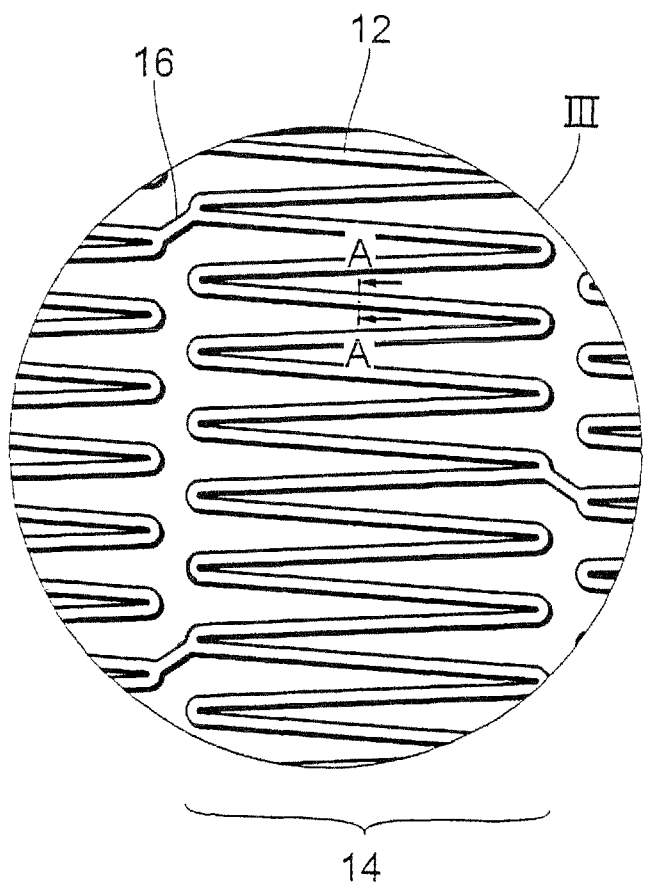
FIG. 2 shows a development of the carrier structure of the stent shown in FIG. 1.

FIG. 2 shows a portion from a development of the peripheral wall of the stent 10. The development shows the compressed condition of the stent 10.

Figure 3:
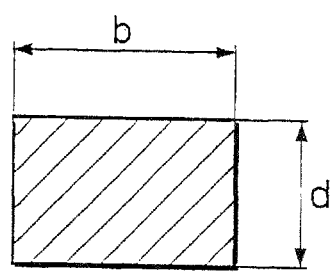
FIG. 3 is a view in cross-section through a leg of the carrier structure of FIG. 2.

FIG. 3 shows the section A-A illustrated in FIG. 2 through a leg 12 of the stent 10. It will be seen that the leg 12 is of a rectangular cross-section and is of a thickness d in the radial direction with respect to the stent. The extent of a leg 12 in the peripheral direction of the stent is the width b.

In preferred embodiments of the stent the legs 12 are all of a substantially similar cross-sectional area so that at least the ratio of largest to smallest cross-sectional area is not greater than two.

The respective smallest extent of the legs 12 of the stent 10—according to b or d—should also be the same for the entire stent in the sense that the ratio of the relatively largest smallest extent of a leg 12 at one location of the stent 10 with respect to the relatively smallest smallest extent of a leg 12 at another location of the stent 10 is less than two.

The connecting legs 16 are of a smaller cross-sectional than the legs 12. They are in particular thinner, that is to say the dimension d is smaller than in the case of the legs 12. The consequence of this is that the connecting legs are the first which are broken down in the body of a patient. As a result axial mobility of the stent increases with the stent still continuing at the same time to provide the supporting action afforded by the leg rings 14. The slower breakdown of the leg rings 14 in comparison with the connecting legs 16 means that the supporting action of the stent 10 decreases more slowly than axial flexibility increases.

The carrier structure of the stent 10 shown in the Figures comprises a magnesium alloy whose magnesium proportion is greater than 90%. In addition the magnesium alloy contains yttrium in a proportion of between 4% and 5% and neodymium as a rare earth element in a proportion of between 1.5% and 4%. The remaining constituents of the alloy are less than 1% and are formed for the major part by lithium or zirconium.

What is claimed is:

1. An endoprosthesis, comprising:
a carrier structure comprising a metallic material;
wherein the metallic material comprises a magnesium alloy of the following composition:

| | |
|---|---|
| Magnesium: | >90% |
| Yttrium: | 3.7%-5.5% |
| Rare earths: | 1.5%-4.4% and |
| Balance: | <1%. |

2. The endoprosthesis of claim 1, wherein:
the yttrium proportion in the magnesium alloy is between 4% and 5%.

3. The endoprosthesis of claim 2, wherein:
the carrier structure consists essentially of the magnesium alloy.

4. The endoprosthesis of claim 2, wherein:
the carrier structure provides a cell survival rate of over about 70 percent upon cultivation of smooth muscle cells with the eluate of the material of the carrier structure in comparison with untreated cells, or a proliferation inhibition effect below about 20 percent with respect to untreated smooth muscle cells.

5. The endoprosthesis of claim 1, wherein:
the rare earths proportion in the magnesium alloy is between 1.5% and 4%.

6. The endoprosthesis of claim 5, wherein:
the carrier structure consists essentially of the magnesium alloy.

7. The endoprosthesis of claim 5 wherein:
the carrier structure provides a cell survival rate of over about 70 percent upon cultivation of smooth muscle cells with the eluate of the material of the carrier structure in comparison with untreated cells, or a proliferation inhibition effect below about 20 percent with respect to untreated smooth muscle cells.

8. The endoprosthesis of claim 1, wherein:
the rare earths proportion in the magnesium alloy comprises neodymium.

9. The endoprosthesis of claim 8, wherein:
the carrier structure consists essentially of the magnesium alloy.

10. The endoprosthesis of claim 8, wherein:
the carrier structure provides a cell survival rate of over about 70 percent upon cultivation of smooth muscle cells with the eluate of the material of the carrier structure in comparison with untreated cells, or a proliferation inhibition effect below about 20 percent with respect to untreated smooth muscle cells.

11. The endoprosthesis of claim 1, wherein:
the balance proportion in the magnesium alloy is formed for the major part by zirconium.

12. The endoprosthesis of claim 11, wherein:
the carrier structure consists essentially of the magnesium alloy.

13. The endoprosthesis of claim 11, wherein:
the carrier structure provides a cell survival rate of over about 70 percent upon cultivation of smooth muscle cells with the eluate of the material of the carrier structure in comparison with untreated cells, or a proliferation inhibition effect below about 20 percent with respect to untreated smooth muscle cells.

14. The endoprosthesis of claim 1, wherein:
the carrier structure consists essentially of the magnesium alloy.

15. The endoprosthesis of claim 14, wherein:
the carrier structure provides a cell survival rate of over about 70 percent upon cultivation of smooth muscle cells with the eluate of the material of the carrier structure in comparison with untreated cells, or a proliferation inhibition effect below about 20 percent with respect to untreated smooth muscle cells.

16. The endoprosthesis of claim 1, wherein:
the carrier structure provides a cell survival rate of over about 70 percent upon cultivation of smooth muscle cells with the eluate of the material of the carrier structure in comparison with untreated cells, or a proliferation inhibition effect below about 20 percent with respect to untreated smooth muscle cells.

17. The endoprosthesis of claim 1, wherein:
the endoprosthesis is in the form of an intraluminal endoprosthesis.

18. The endoprosthesis of claim 17, wherein:
the endoprosthesis is in the form of a stent.

19. The endoprosthesis of claim 18, wherein:
the endoprosthesis is in the form of a coronary stent.

20. The endoprosthesis of claim 19, wherein:
the endoprosthesis is in the form of a self-expanding stent.

21. The endoprosthesis of claim 19, wherein:
the endoprosthesis is in the form of a balloon-expandable stent.

22. The endoprosthesis of claim 18, wherein:
the endoprosthesis is in the form of a self-expanding stent.

23. The endoprosthesis of claim 18, wherein:
the endoprosthesis is in the form of a peripheral stent.

24. The endoprosthesis of claim 23, wherein:
the endoprosthesis is in the form of a self-expanding stent.

25. The endoprosthesis of claim 23, wherein:
the endoprosthesis is in the form of a balloon-expandable stent.

26. The endoprosthesis of claim 18, wherein:
the endoprosthesis is in the form of a balloon-expandable stent.

27. The endoprosthesis of claim 1, wherein:
the carrier structure is produced by cutting a tube from one piece.

28. The endoprosthesis of claim 1, wherein:
the carrier structure is formed from a wire which contains the magnesium alloy.

29. The endoprosthesis of claim 1, wherein:
the carrier structure encloses an elongated hollow space which is open at its ends.

30. The endoprosthesis of claim 29, wherein:
the carrier structure is of a lattice-like structure and is formed by a plurality of legs and radial openings enclosed by said plurality of legs.

31. The endoprosthesis of claim 30, wherein:
the plurality of legs all have a similar cross-sectional area such that a ratio of largest to smallest cross-sectional area is smaller than 2.

32. The endoprosthesis of claim 31, wherein:
a first plurality of the plurality of legs form leg rings and a second plurality of the plurality of legs define connecting legs that connect adjacent leg rings together, wherein the connecting legs are of a smaller cross-sectional area or a smaller minimum diameter than the legs which form the leg rings.

33. The endoprosthesis of claim 30, wherein:

the plurality of legs all have a similar minimum diameter such that a ratio of largest to smallest minimum diameter is less than 2.

34. The endoprosthesis of claim 33, wherein:

a first plurality of the plurality of legs form leg rings and a second plurality of the plurality of legs define connecting legs that connect adjacent leg rings together, wherein the connecting legs are of a smaller cross-sectional area or a smaller minimum diameter than the legs which form the leg rings.

35. The endoprosthesis of claim 30, wherein:

a first plurality of the plurality of legs form leg rings and a second plurality of the plurality of legs define connecting legs that connect adjacent leg rings together, wherein the connecting legs are of a smaller cross-sectional area or a smaller minimum diameter than the legs which form the leg rings.

36. The endoprosthesis of claim 1, wherein:

the endoprosthesis carries a physiologically effective active substance.

37. The endoprosthesis of claim 36, wherein:

the endoprosthesis is coated with at least one drug.

* * * * *